US010035137B2

United States Patent
Paulus et al.

(10) Patent No.: US 10,035,137 B2
(45) Date of Patent: Jul. 31, 2018

(54) HYDROGENATION CATALYST AND PROCESS FOR PRODUCTION THEREOF BY THE USE OF UNCALCINED STARTING MATERIAL

(71) Applicants: Martin Paulus, Rosenheim (DE);
Frank Grossmann, Munich (DE);
Karl-Heinz Stadler, Augsburg (DE)

(72) Inventors: Martin Paulus, Rosenheim (DE);
Frank Grossmann, Munich (DE);
Karl-Heinz Stadler, Augsburg (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

(21) Appl. No.: 14/432,004

(22) PCT Filed: Sep. 25, 2013

(86) PCT No.: PCT/EP2013/069917
§ 371 (c)(1),
(2) Date: Mar. 27, 2015

(87) PCT Pub. No.: WO2014/048957
PCT Pub. Date: Apr. 3, 2014

(65) Prior Publication Data
US 2015/0314273 A1 Nov. 5, 2015

(30) Foreign Application Priority Data

Sep. 28, 2012 (DE) .................. 10 2012 019 123

(51) Int. Cl.
*B01J 33/00* (2006.01)
*B01J 23/889* (2006.01)
(Continued)

(52) U.S. Cl.
CPC .......... *B01J 23/8892* (2013.01); *B01J 23/72* (2013.01); *B01J 33/00* (2013.01); *B01J 35/002* (2013.01);
(Continued)

(58) Field of Classification Search
CPC . B01J 23/72; B01J 33/00; B01J 35/002; B01J 35/1038; B01J 35/1042;
(Continued)

(56) References Cited

U.S. PATENT DOCUMENTS

| 4,386,219 A | 5/1983 | Merger et al. |
| 4,436,833 A | 3/1984 | Broecker et al. |

(Continued)

FOREIGN PATENT DOCUMENTS

| CN | 102407122 | 4/2012 |
| DE | 20 56 612 | 5/1972 |

(Continued)

OTHER PUBLICATIONS

PCT International Search Report for PCT/EP2013/069917, dated Feb. 4, 2014.

(Continued)

*Primary Examiner* — Patricia L. Hailey
(74) *Attorney, Agent, or Firm* — Anthony A. Bisulca

(57) ABSTRACT

The invention relates to a process for preparing a shaped Cu—Al catalyst body for the hydrogenation of organic compounds containing a carbonyl function. More particularly, the shaped catalyst body is suitable for the hydrogenation of aldehydes, ketones and of carboxylic acids or esters thereof, specifically of fatty acids or esters thereof, such as fatty acid methyl esters, to the corresponding alcohols such as butanediol. The present invention further relates to Cu—Al catalysts obtainable by the preparation process.

48 Claims, 1 Drawing Sheet

Pore radius distribution

Pore radius [nm]

(51) Int. Cl.
*B01J 37/18* (2006.01)
*B01J 37/03* (2006.01)
*B01J 37/04* (2006.01)
*B01J 37/08* (2006.01)
*B01J 23/72* (2006.01)
*B01J 35/00* (2006.01)
*B01J 35/10* (2006.01)
*B01J 37/00* (2006.01)
*C07C 29/149* (2006.01)
*B01J 37/06* (2006.01)

(52) U.S. Cl.
CPC ......... *B01J 35/109* (2013.01); *B01J 35/1038* (2013.01); *B01J 35/1042* (2013.01); *B01J 37/0009* (2013.01); *B01J 37/0063* (2013.01); *B01J 37/031* (2013.01); *B01J 37/04* (2013.01); *B01J 37/08* (2013.01); *B01J 37/18* (2013.01); *C07C 29/149* (2013.01); *B01J 37/06* (2013.01)

(58) Field of Classification Search
CPC .. B01J 37/0009; B01J 37/0063; B01J 37/031; B01J 37/04; B01J 37/06; B01J 37/08
USPC ....... 502/304, 305, 318, 324, 329, 331, 345, 502/346, 349, 355, 439, 527.24
See application file for complete search history.

(56) References Cited

U.S. PATENT DOCUMENTS

| | | | |
|---|---|---|---|
| 4,596,782 A | 6/1986 | Courty et al. | |
| 4,666,879 A | 5/1987 | Kelly et al. | |
| 4,762,817 A | 8/1988 | Logsdon et al. | |
| 4,929,771 A | 5/1990 | Clausen et al. | |
| 5,008,235 A | 4/1991 | Wegman et al. | |
| 5,093,534 A | 3/1992 | Ludwig et al. | |
| 5,122,495 A | 6/1992 | Taylor et al. | |
| 5,124,295 A | 6/1992 | Nebesh et al. | |
| 5,134,108 A | 7/1992 | Thakur et al. | |
| 5,155,086 A | 10/1992 | Thakur et al. | |
| 5,334,779 A * | 8/1994 | Kuo .................... | B01J 23/80 568/830 |
| 5,345,005 A | 9/1994 | Thakur et al. | |
| 5,346,005 A | 9/1994 | Thakur et al. | |
| 5,536,694 A | 7/1996 | Schuetz et al. | |
| 6,337,300 B1 | 1/2002 | Sauer et al. | |
| 6,627,572 B1 * | 9/2003 | Cai .................... | B01J 23/80 502/307 |
| 6,787,677 B2 * | 9/2004 | Koch .................. | B01J 23/72 502/103 |
| 6,888,011 B2 | 5/2005 | Borchert et al. | |
| 7,119,237 B2 * | 10/2006 | Prinz .................. | B01J 23/80 502/342 |
| 7,759,530 B2 * | 7/2010 | Houssin ............. | B01J 23/002 502/303 |
| 2007/0117719 A1 * | 5/2007 | Schlitter ............. | B01J 23/72 502/345 |
| 2015/0238938 A1 | 8/2015 | Paulus et al. | |
| 2017/0113209 A1 | 4/2017 | Paulus et al. | |
| 2017/0252727 A1 | 9/2017 | Paulus et al. | |

FOREIGN PATENT DOCUMENTS

| | | | | |
|---|---|---|---|---|
| DE | 30 27 890 | | 3/1982 | |
| DE | 43 35 360 | | 4/1995 | |
| DE | 43 45 265 | | 9/1995 | |
| DE | 10 2005 049135 | | 4/2007 | |
| DE | 10 2011 0864 | | 5/2013 | |
| EP | 0 011 150 | | 5/1980 | |
| EP | 880 996 | | 12/1996 | |
| EP | 1 338 587 | * | 8/2003 | ........... C07C 29/149 |
| GB | 1 366 367 | | 9/1974 | |
| WO | WO 92/04119 | | 3/1992 | |
| WO | 97/34694 | * | 9/1997 | ............. B01J 23/72 |
| WO | WO 97/34694 | | 9/1997 | |
| WO | WO 02/47818 | | 6/2002 | |
| WO | 2006/005505 | * | 1/2006 | ........... B01J 23/885 |
| WO | WO 2006/005505 | | 1/2006 | |
| WO | WO 2013/072197 | | 6/2013 | |

OTHER PUBLICATIONS

International Preliminary Report on Patentability for PCT/EP2013/069917, dated Mar. 31, 2015.
Machine Translation for DE 10 2005 049135, Apr. 19, 2007.
Abstract Machine Translation for WO 92/04119, Mar. 19, 1992.
Machine Translation for CN 102407122, Apr. 11, 2012.
U.S. Appl. No. 15/508,231 entitled "Extruded Cu—Al—Mn Hydrogenation Catalyst" by Paulus et al., filed with the United States Patent and Trademark Office on Mar. 2, 2017.
PCT International Search Report or PCT/EP2015/055758, dated Jul. 7, 2015.
PCT International Preliminary Report on Patentability for PCT/EP2015/055758, dated Sep. 27, 2016.
G.C. Chinchen et al. "The Measurement of Copper Surface Areas by Reactive Frontal Chromatography", Journal of Catalysts, vol. 103, Issue 1, pp. 79-86, Jan. 1987.
United states Patent and Trademark Office Office Action for U.S. Appl. No. 15/128,700 dated Apr. 27, 2017.

* cited by examiner

HYDROGENATION CATALYST AND PROCESS FOR PRODUCTION THEREOF BY THE USE OF UNCALCINED STARTING MATERIAL

The invention relates to a process for producing a shaped Cu—Al catalyst body for the hydrogenation of organic compounds containing a carbonyl function, and also the catalysts which can be obtained using this process. The catalyst is particularly suitable for the hydrogenation of aldehydes, ketones and of carboxylic acids and esters thereof, especially fatty acids and esters thereof, e.g. methyl esters of fatty acids, to form the corresponding alcohols, e.g. butanediol.

BACKGROUND OF THE INVENTION

The hydrogenation of carbonyl compounds, in particular of carboxylic acids or carboxylic esters, with the aid of heterogeneous catalysts plays an important role in the chemical industry. In principle, both slurry applications and fixed-bed applications are possible for these hydrogenations, with fixed-bed applications predominating. In the slurry process, the catalysts are used as a powder, whereas shaped catalyst bodies are used in the fixed-bed processes.

Ni-, Cu-, Co- or noble metal-containing catalysts, in particular, are used for the hydrogenation of carbonyl compounds. These can be used as all-active catalysts (e.g. Raney catalysts) or as supported catalysts.

The patent documents DE 43 45 265 and DE 43 35 360 describe shaped Raney catalysts based on Ni, Co, Cu and Fe. These are used for the hydrogenation of organic compounds. A disadvantage of these catalysts results from the addition of metal powder as binder, with the added metal powder having a lower catalytic activity than the Raney metal.

The production of shaped Raney catalysts without addition of binders is described in EP 880 996. These catalysts are used for the hydrogenation of nitriles. To produce these catalysts, a metal-aluminum alloy present as powder is mixed with a high molecular weight polymer and optionally promoters and subsequently is shaped to give shaped bodies. The shaped bodies are calcined at temperatures of up to 850° C., which leads to controlled decomposition of the polymer and formation of a fixed-bed catalyst having satisfactory mechanical stability. Activation is effected by leaching out the aluminum using sodium hydroxide solution. However, the leaching out of the aluminum and thus activation of the catalyst occurs merely in the outer shell of the shaped body. The core of the catalyst continues to consist of the metal-aluminum alloy used and serves as support for the activated outer layer of the catalyst. As a result, a considerable proportion of the relatively expensive alloys remains unused.

The hydrogenation of carbonyl compounds is carried out using not only the Raney catalysts but also essentially Cu and Ni catalysts supported on various metal oxides such as $Al_2O_3$ or $SiO_2$.

Thus, for example, U.S. Pat. No. 4,666,879 describes an extruded copper chromite-aluminum oxide catalyst which is produced by mixing from 40 to 82% by weight of copper chromite and from 18 to 60% by weight of aluminum oxide. The $Al_2O_3$ is typically used in the form of pseudoboehmite or hydroxyboehmite. The extruded catalyst is, after calcination, suitable for the liquid- and gas-phase hydrogenation and hydrogenolysis of various carbonyl compounds and functional side groups of aromatic compounds. The BET surface area of the extruded catalyst is typically in the range from 125 to 225 $m^2/g$.

U.S. Pat. No. 4,762,817 describes a catalyst for the hydrogenation of aldehydes, which consist essentially of a mixture of copper and zinc oxide. An improvement in the selectivity was able to be achieved by impregnation with alkali metals such as sodium, potassium, lithium or cesium in combination with a transition metal such as nickel, cobalt or mixtures thereof.

The U.S. Pat. No. 4,929,771 describes catalyst compositions containing oxides of Cu and Ti and the use of such catalyst compositions in the hydrogenation of particular esters to form the corresponding alcohols.

The U.S. Pat. No. 5,008,235 describes a process for the hydrogenation of organic aromatic or nonaromatic acids and esters thereof to form the corresponding alcohols using a coprecipitated catalyst. The catalyst contains copper, aluminum and a further metal such as magnesium, zinc, titanium, zirconium, tin, nickel, cobalt or mixtures thereof and is subjected to reduction before use. The temperature in the reduction is increased stepwise to a final temperature of from 150° C. to 250° C.

The U.S. Pat. No. 5,093,534 describes a two-stage process for the hydrogenation of saturated and unsaturated aldehydes to alcohols using Cu- and Ni-containing catalysts. The first stage of the hydrogenation is carried out using a particulate alkaline copper catalyst. In the second stage of the hydrogenation, a supported nickel-containing catalyst whose support material has acidic sites having a particular acid strength is used.

The U.S. Pat. No. 5,124,295 describes an extruded copper chromite catalyst consisting of a mixture containing from about 20 to 80% by weight of copper chromite and from about 20 to 80% by weight of an extrudable inorganic binder. The catalyst has a specific surface area of from about 20 to 225 $m^2/g$, and the total pore volume of the pores in the catalyst is from 0.35 to 1 $cm^3/g$. In one embodiment, this document describes a process for producing a shaped copper chromite catalyst by production of an extrudable mixture, extrusion of the mixture and calcination of the extrudate. The catalysts are employed for the hydrogenation of aldehydes, ketones, carboxylic acids and carboxylic esters.

The U.S. Pat. No. 5,134,108 describes a hydrogenation catalyst comprising oxides of a first metal, copper or zinc, and a second metal, chromium, molybdenum, tungsten or vanadium, and optionally an oxide of a promoter such as manganese, barium, zinc, nickel, cobalt, cadmium or iron. The hydrogenation catalyst is in the form of a powder whose average particle diameter is from about 6 to 20 μm and whose surface area is from about 20 to 70 $m^2/g$. The catalysts are produced by precipitation of the metal salts by means of a base.

U.S. Pat. No. 5,155,086 and U.S. Pat. No. 5,345,005 describe a pulverulent catalyst which consists largely of the oxides of copper and zinc and a smaller proportion of aluminum oxide, where the atomic ratio of copper to zinc is from 0.2 to 5.5. The catalyst is produced by precipitation, e.g. at a pH of >7, and calcination of the precipitate. The hydrogenation catalysts are used for the hydrogenation of aldehydes, ketones, carboxylic acids and carboxylic esters.

WO 92/04119 describes copper-manganese catalysts for the hydrogenation of fatty acids and esters thereof. They are produced by admixing an aqueous solution of Cu(II) and Mn(II) salts with sodium hydroxide solution, forming a precipitate of Cu hydroxide and Mn hydroxide. This precipitate is then calcined as powder or in tableted form. The catalysts obtained have a BET surface area of from about 3 to 45 m²/g.

WO 02/47818 describes Cu oxide-containing catalysts for the hydrogenation of maleic anhydride and derivatives thereof. As pore formers, use is made here of, in particular, graphite and ammonium nitrate which are mixed into the catalyst powder before tableting. The catalysts in the production of which exclusively graphite was used as pore former had a pore volume of less than 0.2 cm³/g.

WO 97/34694 describes copper oxide/aluminum oxide hydrogenation catalysts produced by precipitation of aqueous solutions of copper nitrate and sodium aluminates using sodium carbonate. The material obtained is, after drying, calcined at from about 400° C. to 700° C. and subsequently tableted with addition of graphite. The pellets have a pore volume of from 0.2 to 0.6 ml/g and a bimodal pore radius distribution having a first maximum at about 10 nm and a second maximum at from about 50 to not more than 200 nm.

In the commercial use of catalysts, an increase in the conversion to the target product, in particular, is of greatest interest in the context of a further improvement in the economics. Pellet-shaped catalysts are predominantly used for hydrogenation reactions. These usually have a higher mechanical stability than, for example, extrudates. The stability is a consequence of the process of tableting since relatively high pressures normally prevail there. However, the pore volume and thus the accessibility of the active sites is frequently reduced by the strong compression during tableting, which has an adverse effect on the conversion in catalytic reactions. To compensate for this disadvantage, pore formers are frequently added during the production of tableted catalysts in the prior art in order to achieve an increase in the pore volume. However, the addition of pore formers incurs the risk that the active catalyst material will be adversely affected by additives. Particularly when using organic pore formers which are burnt out from the catalyst in order to increase the pore volume, carbonization of the surface can take place. In addition, additives, whether organic or inorganic, always involve the risk that impurities and catalysts poisons will be introduced into the catalyst. A further disadvantage of burn-out materials as pore formers is the often very locally arising evolution of heat during burning-out. The active sites are often adversely affected thereby. In particular, sintering effects and a decrease in the dispersion of metal particles and thus a reduction in the activity of the catalysts can occur.

In view of this background, it was an object of the present invention to provide a process for producing tableted catalysts having an increased pore volume, without any pore formers being added.

A further object was to provide tableted catalysts which have a higher activity in hydrogenation reactions compared to catalysts of the prior art.

This object is achieved by the process of the invention and the catalysts obtainable thereby.

SUMMARY OF THE INVENTION

The invention provides a process for producing a tableted shaped catalyst body, which comprises the following steps:
(a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate, and (b) tableting of the dried precipitate obtained in step (a) to give the tableted shaped catalyst body.

The process further provides a process in which part of the dried precipitate obtained in step (a) is calcined in a step (b1) and the calcined precipitate obtained from step (b1) is subsequently, in a step (b2), mixed with part of the dried precipitate obtained in step (a) and the resulting mixture is tableted in a step (b3).

The invention also provides a process in which the tableted shaped body obtained in step (b) or in step (b3) is after-calcined in a step (c).

Furthermore, the invention provides Cu—Al catalysts which can be produced by the processes of the invention.

The invention additionally provides for the use of Cu—Al catalysts according to the invention for the hydrogenation of organic compounds, in particular compounds containing a carbonyl function.

DETAILED DESCRIPTION OF THE INVENTION

In a first embodiment, the process of the invention comprises the following steps for producing a tableted shaped catalyst body:
(a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated (optionally washed) precipitate to give a dried precipitate, and
(b) tableting of the dried precipitate obtained in step (a).

In a second embodiment, the process of the invention comprises the following steps:
(a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated (optionally washed) precipitate to give a dry precipitate, and
(b1) calcination of part of the dried precipitate obtained in step (a) at a temperature in the range from 250 to 900° C., preferably at a temperature in the range from 300 to 750° C., particularly preferably at a temperature in the range from 600 to 750° C., to give a calcined precipitate,
(b2) mixing of part of the precipitate obtained in step (a) with calcined precipitate obtained in step (b1) in a weight ratio of dried precipitate (a) to calcined precipitate (b1) in the range from 2:98 to 98:2, preferably in the range from 10:90 to 90:10, more preferably in the range from 15:85 to 85:15 and particularly preferably in the range from 20:80 to 50:50, to give a mixture, and
(b3) tableting of the mixture obtained in step (b2) to give a tableted shaped catalyst body.

This second embodiment differs from the first embodiment in that part of the dried precipitate obtained in step (a) is calcined and mixed with part of the dried (uncalcined) precipitate obtained in step (a) before tableting.

In the process of the invention for producing a tableted shaped catalyst body, at least one aqueous solution of copper compounds, aluminum compounds and optionally transition metal compounds and at least one aqueous carbonate-containing solution are firstly provided.

The formulation "aqueous solution of copper compounds, aluminum compounds and optionally transition metal compounds" as used for the purposes of the present invention includes both aqueous solutions and aqueous suspensions and aqueous slurries of the copper compounds, aluminum compounds and optionally transition metal compounds, with aqueous solutions being preferred. The at least one aqueous solution of copper compounds, aluminum compounds and optionally transition metal compounds is, for example, produced by dissolving, suspending and/or slurrying, preferably dissolving, at least one copper compound, at least one aluminum compound and optionally one or more transition metal compounds in water at an acidic, neutral or basic pH, preferably at an acidic or neutral pH.

As copper compounds and aluminum compounds, it is in principle possible to use either copper and aluminum in metallic form or preferably all compounds of copper and aluminum which are readily soluble in water, acids or alkalis, in particular the salts of the metals mentioned, very particularly preferably their nitrates, carbonates, oxides, hydroxides, hydroxocarbonates, halides such as chlorides, bromides and/or iodides and/or sulfates. When oxides of the metals, e.g. copper oxide and/or aluminum oxide, are used for producing the aqueous solutions, these are preferably partly or completely dissolved by addition of a suitable mineral acid. The copper in copper oxide can be present in one or more different oxidation states, e.g. copper (I) oxide, copper (II) oxide and mixtures thereof. The mineral acid is preferably selected from among $HNO_3$, HCl, $H_2SO_4$ and mixtures thereof. When the metals themselves, i.e. copper and/or aluminum, are used for producing the aqueous solution(s), suspension(s) or slurry(ies), then these are preferably partly or completely dissolved by addition of suitable acids or alkalis. The dissolution of the metals can, for example, be effected in inorganic acids or alkalis.

Preferred copper compounds are copper oxide ($Cu_2O$ and/or CuO), copper nitrate, copper chloride, copper carbonate, copper hydroxocarbonate ($x.CuCO_3.Cu(OH)_2$, where x can be 1 or 2), copper acetate and copper sulfate, in particular copper nitrate. As an alternative, copper metal can also be dissolved in oxidizing acids such as nitric acid ($HNO_3$).

Preferred aluminum compounds are aluminum nitrate, aluminum hydroxide, aluminum oxide hydrate (boehmite), aluminum chloride, alkali metal aluminates and aluminum oxide ($Al_2O_3$), in particular aluminum nitrate and Na aluminate. As an alternative, aluminum metal can also be dissolved in nonoxidizing acids such as hydrochloric acid (HCl) or in alkalis such as sodium hydroxide (NaOH) or potassium hydroxide (KOH).

The transition metal compounds are preferably selected from among compounds of the transition metals zinc, silicon, titanium, manganese, nickel, chromium, iron, cobalt, molybdenum, calcium, barium, cerium, zirconium and mixtures thereof. Particularly preferred transition metal compounds are the compounds of manganese, zinc and mixtures thereof. Very particularly preferred transition metal compounds are the compounds of manganese.

As transition metal compounds, it is in principle possible to use all compounds of zinc, silicon, titanium, manganese, nickel, chromium, iron, cobalt, molybdenum, calcium, barium, cerium and/or zirconium which are readily soluble in water, acids or alkalis, in particularly salts of these metals. Instead of or together with the transition metal compounds, it is also possible to use the transition metals in metallic form. Preference is given to using compounds of Mn, Zn, Ce and/or Zr. The nitrates of these metals, e.g. manganese nitrate, zinc nitrate, cerium nitrate and/or zirconium nitrate, the halides of these metals, e.g. manganese, zinc, cerium and/or zirconium chloride, bromide and/or iodide, the oxides of these metals, e.g. manganese, zinc, cerium and/or zirconium oxides, and/or sulfates of these metals, e.g. manganese sulfate, zinc sulfate, cerium sulfate and/or zirconium sulfate, are preferably used. Greater preference is given to the transition metal compounds selected from the group consisting of manganese nitrate, manganese chloride, cerium nitrate, zinc chloride, zirconium chloride and mixtures thereof. Particular preference is given to manganese nitrate and manganese chloride, in particular manganese nitrate. When the oxides of the abovementioned transition metals are used, the transition metals can be present in one oxidation state or in a plurality of different oxidations states in the oxides. When the transition metals and/or the oxides of the transition metals, e.g. manganese, zinc, cerium and/or zirconium oxides, are used for producing the aqueous solutions of transition metal compounds, then these are preferably partly or completely dissolved by addition of a suitable mineral acid. For example, manganese or manganese oxide, e.g. MNO, $Mn_2O_3$, $Mn_3O_4$, $MnO_2$, $Mn_2O_7$ or mixtures thereof, can be dissolved in hydrochloric acid.

The at least one aqueous solution of copper compounds, aluminum compounds and optionally transition metal compounds can be provided in the form of a plurality of separate aqueous solutions of copper compounds, aluminum compounds and optionally transition metal compounds. For example, one or more aqueous solutions of copper compounds, one or more aqueous solutions of aluminum compounds and optionally one or more aqueous solutions of transition metal compounds can be provided. As an alternative, it is also possible to provide one or more joint aqueous solutions. These can be produced by dissolving copper compounds and/or aluminum compounds and/or optionally transition metal compounds in a common vessel. Combining of separate solutions as described above to form a joint solution is likewise possible.

The aqueous carbonate-containing solution is preferably produced by dissolving at least one alkali metal carbonate (e.g. lithium carbonate, sodium carbonate, potassium carbonate, rubidium carbonate or cesium carbonate), alkaline earth metal carbonate, e.g. magnesium carbonate, calcium carbonate, strontium carbonate or barium carbonate) or ammonium carbonate or mixtures thereof in water. It is likewise possible to use the corresponding hydrogen carbonates or any mixtures of carbonates and hydrogen carbonates together with or instead of the carbonates.

Preference is given to using alkali metal carbonates, ammonium carbonates, alkali metal hydrogen carbonates, ammonium hydrogen carbonates or mixtures thereof, particularly preferably alkali metal carbonates and/or alkali metal hydrogen carbonates.

Preferred alkali metal carbonates are sodium carbonate and potassium carbonate, in particular sodium carbonate. Preferred alkali metal hydrogen carbonates are sodium hydrogen carbonate and potassium hydrogen carbonate, in particular sodium hydrogen carbonate. Particular preference is given to using sodium carbonate and/or sodium hydrogen carbonate.

Combining of the at least one aqueous solution of copper compounds, aluminum compounds and optionally transition metal compounds with the at least one aqueous carbonate-containing solution results in formation of a precipitate. The precipitate is isolated, optionally washed and/or dried and subsequently converted by tableting into a tableted shaped body.

In one embodiment, the combining in step (a) can be effected by introducing the at least one aqueous solution of copper compounds, aluminum compounds and optionally transition metal compounds (either in separate solutions and/or in one or more joint solutions and/or as solution mixture) and the at least one aqueous carbonate-containing solution simultaneously into a common vessel, for example a precipitation vessel. Here, the at least two solutions are preferably introduced continuously into the reaction volume of a precipitation mixer.

In a further embodiment, the combining in step (a) can also be effected by adding the at least one aqueous solution of copper compounds, aluminum compounds and optionally transition metal compounds (either in separate solutions and/or in one or more joint solutions and/or as solution mixture) to the at least one aqueous carbonate-containing solution which has been initially placed, for example, in one or more vessels, e.g. one or more precipitation vessels.

In another embodiment, the combining in step (a) can also be effected by adding the at least one aqueous carbonate-containing solution to the at least one aqueous solution of copper compounds, aluminum compounds and optionally transition metal compounds which has been initially placed, for example, in one or more vessels, e.g. one or more precipitation vessels.

The at least one aqueous solution of copper compounds, aluminum compounds and optionally transition metal compounds is preferably heated to a temperature above 20° C., for example to a temperature in the range from 50° C. to 90° C., in particular to about 80° C., and preferably stirred before the combining step.

Likewise, the at least one carbonate-containing solution is preferably heated to a temperature above 20° C., for example to a temperature in the range from 50° C. to 90° C., in particular to about 80° C., and stirred before the combining step.

In a preferred embodiment, both the at least one aqueous solution of copper compounds, aluminum compounds and optionally transition metal compounds and the at least one carbonate-containing solution are heated to a temperature in the range from 50° C. to 90° C., in particular to about 80° C., and stirred.

On combining of the at least one aqueous solution of copper compounds, aluminum compounds and optionally transition metal compounds with the at least one aqueous carbonate-containing solution, a precipitate is formed in the mixture (hereinafter also referred to as precipitate-containing solution mixture). The combining of the solutions is generally effected in a stirred vessel. The vessel is preferably stirred by means of an inclined-blade stirrer, propeller stirrer or other commercial stirrers.

In a preferred embodiment, the combining of the solutions in step (a) is effected by adding volume streams of aqueous solutions of copper compounds, aluminum compounds and optionally transition metal compounds to the aqueous carbonate-containing solution in a precipitation vessel. The aqueous solutions of copper compounds, aluminum compounds and optionally transition metal compounds can be added as separate solutions and/or as one or more joint solutions.

The precipitate-containing solution mixture is preferably maintained at a temperature above 20° C. and in particular at a temperature in the range from 50° C. to 90° C., preferably about 80° C. In a particularly preferred embodiment of the invention, the precipitate-containing solution mixture is maintained for at least 30 minutes, preferably from 1 to 36 hours, in particular about 2 hours, at a temperature in the range from 50° C. to 90° C., preferably at a temperature of about 80° C., in order to possibly complete precipitate formation or increase the crystallinity of the precipitate by ageing.

The pH of the mixture is preferably kept in the range from 5.0 to 8.5, in particular in the range from 6.0 to 7.5, preferably at about 6.8, during the entire time.

The precipitate is preferably isolated by filtration. As an alternative, the precipitate can also be isolated by decantation or centrifugation. The isolated precipitate is subsequently subjected to drying. Drying can, for example, be effected by spray drying. For this purpose, a suspension having a solids content of from 10 to 40% by weight is produced from the isolated precipitate, e.g. a filter cake, using water. This suspension is then preferably fed into a spray dryer via a nozzle. The temperature in the spray dryer during drying is preferably in the range from 75° C. to 130° C., in particular in the range from 90° C. to 120° C. The outlet temperature characteristic for the drying is preferably in the range from 90° C. to 120° C. and is usually controlled by means of parameters such as amount of suspension sprayed in, the solids content of the suspension (and thus the amount of water which has to be evaporated) or temperature in the spray dryer. The treatment of the material by means of the spray dryer results, in particular, in a dry powder.

The isolated precipitate can optionally be subjected to one or more washing steps before drying. Here, the precipitate-containing solution mixture can firstly be separated off from the precipitate using a filter press and water can subsequently be passed through the material in the filter press, thus washing the material. As an alternative, the isolated precipitate can, after removal of the precipitate-containing solution mixture by filtration, decantation or centrifugation, be slurried in a vessel and subsequently once again separated from the liquid phase by means of a filter press, a centrifuge or a decanter. This operation is generally carried out one or more times until a particular conductivity of the filtrate has been achieved. Here, the conductivity generally correlates with the concentration of sodium ions. The conductivity of the filtrate from the last washing operation is preferably 0.5 mS/cm or less, in particular 0.2 mS/cm or less. The conductivity is determined in accordance with DIN 38404, part 8.

The dried precipitate obtained in the above-described step (a) is subsequently tableted (with part of the precipitate being able to be calcined beforehand). Tableting is preferably carried out using a tableting press, for example a Korsch tableting press. Tableting makes it possible to obtain pellets having a diameter of from about 1 to 10 mm, preferably from 1.5 to 8 mm and particularly preferably from 3 to 5 mm, and a height of from about 1 to 10 mm, preferably from 1.5 to 8 mm and particularly preferably from 3 to 5 mm. In particular, pellets having a lateral compressive strength, measured in accordance with DIN EN 1094-5, of from 40 to 250 N, preferably from 50 to 160 N, particularly preferably from 60 to 120 N, are produced. The pellets produced by tableting preferably have a diameter in the range from 3 to 5 mm, a height in the range from 3 to 5 mm and a lateral compressive strength in the range from 60 to 120 N.

Tableting is preferably carried out with addition of lubricants such as graphite, oils or stearates, preferably graphite. Here, the dried precipitate obtained in step (a) is mixed with lubricants, in particular graphite, optionally compacted and/or granulated and then tableted. The lubricant is preferably added in an amount in the range from 0.1 to 5% by weight, based on the total weight of the composition to be tableted, before tableting. The lubricant is more preferably added in an amount in the range from 0.5 to 5% by weight, particularly preferably in an amount in the range from 1 to 4% by weight, based on the total weight of the composition to be tableted.

In one embodiment, part of the dried precipitate obtained in step (a) is subjected to calcination in a step (b1) before tableting. This calcined precipitate obtained in step (b1) is then mixed with dried (uncalcined) precipitate obtained in step (a) in a step (b2) and the mixture obtained is subsequently tableted as described above, optionally with addition of lubricants, in a step (b3).

The calcination in step (b1) is effected by means of a thermal treatment in which the temperature is in the range from 250° C. to 900° C., preferably in the range from 300° C. to 750° C., particularly preferably in the range from 600° C. to 750° C. The calcination can be carried out in air or under protective gas, for example argon or nitrogen, under oxygen or mixtures thereof. The calcination can be carried out batchwise, e.g. in a tray furnace, or continuously, e.g. in a rotary tube furnace. Calcination in a rotary tube furnace can be controlled by means of the residence time and different heating zones. The rotary tube furnace preferably has from one to ten different heating zones, in particular about five heating zones. The temperature in the various heating zones is, for example, in the range from 300° C. to 400° C. for the first heating zone, in the range from 500° C. to 600° C. for the second heating zone, in the range from 600° C. to 750° C. for the third heating zone, in the range from 650° C. to 800° C. for the fourth heating zone and in the range from 500° C. to 700° C. for the fifth heating zone. The residence time in the various heating zones is preferably in the range from 5 minutes to 60 minutes, in particular in the range form 10 minutes to 30 minutes. When a tray furnace is used, the dried precipitate obtained from step (a) is usually spread out on metal trays. In the tray furnace, temperature profiles can be achieved by means of appropriate furnace control. The temperature profile can, for example, comprise heating at a heating rate of 2° C./min from 20° C. to 750° C., holding at 750° C. for three hours and cooling at a cooling rate of 2° C./min to 20° C.

The calcined precipitate obtained in step (b1) consists to an extent of from 85% by weight or more, preferably 92% by weight or more, particularly preferably 95% by weight or more, based on the weight of the calcined precipitate, essentially of, in particular, oxidic constituents. For example, the calcined precipitate obtained in step (b1) can consist to an extent of from 96 to 99.5% by weight, based on the weight of the calcined precipitate, of oxidic constituents. The oxidic constituents comprise oxides of the metals and/or transition metals used, e.g. copper oxide, aluminum oxide, zinc oxide, silicon oxide, titanium oxide, manganese oxide, nickel oxide, chromium oxide, iron oxide, cobalt oxide, molybdenum oxide, calcium oxide, barium oxide, cerium oxide, zirconium oxide and mixtures thereof. Each metal and/or transition metal can be present independently in various stoichiometric compositions with the oxygen. Each metal and/or transition metal can be present independently in one or more different oxidation states.

The calcined precipitate obtained in step (b1) has a carbonate content (i.e. content of $CO_3^{2-}$) of 8% by weight or less, particularly preferably 5% by weight or less, for example from 0.5 to 4% by weight, based on the total weight of the calcined precipitate obtained in step (b1).

In contrast thereto, the dried uncalcined precipitate obtained in step (a) preferably consists essentially of metal carbonates or hydroxocarbonates or hydroxides or mixtures thereof. The uncalcined precipitate consists to an extent of 20% by weight or less, preferably 10% by weight or less, particularly preferably 5% by weight or less, for example from 0.5 to 4% by weight, based on the weight of the uncalcined precipitate, of oxidic constituents.

The dried uncalcined precipitate obtained in step (a) preferably has a carbonate content of up to 20% by weight, preferably in the range from 5% by weight to 18% by weight, particularly preferably in the range from 6% by weight to 15% by weight and very particularly preferably in the range from 8 to 12% by weight. The carbonates present in the uncalcined precipitate are, in the case of copper carbonate, present mainly in the form of copper hydrocarbonate ($x \cdot CuCO_3 \cdot Cu(OH)_2$, where x=1 or 2), or generally as mixed carbonates and hydroxocarbonates of the metal components used.

The calcined precipitate obtained by the calcination in step (b1) is, in step (b2), mixed with dried uncalcined precipitate obtained in step (a) in a weight ratio of uncalcined precipitate to calcined precipitate in the range from 2:98 to 98:2, preferably in the range from 10:90 to 90:10, more preferably in the range from 15:85 to 85:15 and particularly preferably in the range from 20:80 to 50:50. The mixture of uncalcined and calcined precipitate obtained is subsequently tableted as described above, optionally with addition of lubricants.

In a further embodiment, the shaped catalyst body is produced by tableting a mixture of oxidic material and carbonate-containing material. The oxidic material comprises oxides of the metals and/or transition metals used, e.g. copper oxide, aluminum oxide, zinc oxide, silicon oxide, titanium oxide, manganese oxide, nickel oxide, chromium oxide, iron oxide, cobalt oxide, molybdenum oxide, calcium oxide, barium oxide, cerium oxide, zirconium oxide and mixtures thereof. Each metal and/or transition metal can be present independently in various stoichiometric compositions with the oxygen. Each metal and/or transition metal can be present independently in one or more different oxidation states. The carbonate-containing material comprises carbonates of the metals and/or transition metals used, e.g. copper carbonate, aluminum carbonate, zinc carbonate, silicon carbonate, titanium carbonate, manganese carbonate, nickel carbonate, chromium carbonate, iron carbonate, cobalt carbonate, molybdenum carbonate, calcium carbonate, barium carbonate, cerium carbonate, zirconium carbonate and mixtures thereof. The various components such as oxides and/or carbonates can also originate from different production processes or have been produced by different production routes or, for example, be commercially available raw materials.

In a further preferred embodiment, the tableted shaped body which has been obtained in step (b) and in whose production no calcined precipitate was added (i.e. the shaped body obtained by tableting of dried uncalcined precipitate) or the tableted shaped body which has been obtained in step (b3) and in whose production calcined and uncalcined precipitate was mixed in the abovementioned weight ratios is subjected to an additional heat treatment in a step (c).

This additional heat treatment will in the present text also be referred to as after-calcination. In this heat treatment, the carbonate-containing uncalcined precipitate obtained in the pellet is converted into a corresponding oxidic form. The after-calcination of the tableted shaped catalyst body is carried out at a temperature in the range from 250° C. to 900° C., preferably at a temperature of from 300° C. to 750° C., particularly preferably from 600° C. to 750° C. The after-calcination can be carried out batchwise or continuously, e.g. in a belt calciner or a tray furnace. The heat treatment is preferably carried out in an atmosphere selected from among air, nitrogen, argon, carbon dioxide or mixtures thereof. The heat treatment is preferably carried out over a period of from 30 minutes to 8 hours, preferably over a period of from 1 to 6 hours. The after-calcined pellet obtained in step (c) preferably has a carbonate content of 2% by weight or less.

The remaining loss on ignition at 1000° C. of the catalysts of the invention is 5% by weight or less, preferably 3% by weight or less, for the after-calcined pellets. The remaining loss on ignition is determined in accordance with DIN EN 196-2.

In a further embodiment, the tableted shaped catalyst body obtained from steps (b) or (b3) is reduced in a step (d), with this tableted shaped catalyst body being able to be after-calcined beforehand in step (c).

Reduction is preferably carried out by heating of the tableted shaped catalyst body or the after-calcined shaped catalyst body in a reducing atmosphere. In particular, the reducing atmosphere is hydrogen. Reduction is carried out, for example, at a temperature in the range from 150° C. to 450° C., in particular in the range from 180° C. to 250° C., preferably in the range from 190° C. to 210° C., particularly preferably at about 200° C. Reduction is, for example, carried out over a period of from 1 hour to 10 days, in particular over a period of from 2 hours to 72 hours, preferably over a period of from 24 to 48 hours. In a preferred embodiment, reduction is carried out at a temperature in the range from 190° C. to 210° C. over a period of from 24 to 48 hours.

The shaped catalyst bodies are preferably stabilized wet or dry after reduction. In the case of wet stabilization, the shaped bodies are covered with liquid in order to avoid contact with oxygen as far as possible. Suitable liquids include organic liquids and water, preferably organic liquids. Preferred organic liquids are those which have a vapor pressure of 0.5 hPa or less at 20° C., Examples of suitable organic liquids are isodecanol, Nafol, fatty alcohols, hexadecane, 2-ethylhexanol, propylene glycol and mixtures thereof, in particular isodecanol.

In the case of dry stabilization, a mixture of oxygen or an oxygen-containing gas, preferably air, and an inert gas such as argon or nitrogen is introduced into the reduction reactor. The concentration of oxygen in the mixture is preferably increased from about 0.04% by volume to about 21% by volume. For example, it is possible to introduce a mixture of air and inert gas in which the ratio of air to inert gas is initially about 0.2% by volume of air to 99.8% by volume of inert gas. The ratio of air to inert gas is then gradually increased (e.g. continuously or stepwise) until, for example, 100% by volume of air (which corresponds to an oxygen concentration of about 21% by volume) is fed in at the end. Without being tied to a theory, it is presumed that a thin oxide layer having a thickness of, for example, from 0.5 to 50 nm, preferably from 1 to 20 nm, in particular from 1 to 10 nm, is formed on the surface of the catalyst as a result of the introduction of air or oxygen and protects the catalyst against further oxidation. In the case of dry stabilization, the reactor temperature is preferably 100° C. or less, more preferably from 20° C. to 70° C. and particularly preferably from 30° C. to 50° C. After this stabilization, the catalyst is "transportable" and can be transported to the user/plant operator. When the catalyst user carries out step (c) in-situ in the reactor, stabilization is dispensed with.

The shaped catalyst bodies of the invention or the shaped catalyst bodies obtainable by the process of the invention contain Cu (i.e. copper in the oxidation state 0), in particular in a proportion of from 5 to 70% by weight, preferably in a proportion of from 10 to 70% by weight, particularly preferably in a proportion of from 20 to 50% by weight, based on the total weight of the shaped catalyst body, after reduction.

The shaped catalyst bodies of the invention or the shaped catalyst bodies obtainable by the process of the invention preferably have a bimodal pore radius distribution. The bimodal pore radius distribution preferably has a first maximum in the range from 10 to 30 nm, more preferably in the range from 15 to 25 nm, in particular at about 20 nm, and/or a second maximum in the range from 500 to 2500 nm, more preferably in the range from 700 to 2000 nm, in particular in the range from about 800 to 1000 nm. The bimodal pore radius distribution preferably has a first maximum in the range from 15 to 25 nm and a second maximum in the range from 700 to 2000 nm. The bimodal pore radius distribution more preferably has a first maximum at about 20 nm and a second maximum in the range from 800 to 1000 nm.

Preference is given to from 5 to 30%, more preferably from 10 to 25%, in particular from 15 to 25%, of the pore volume of the shaped catalyst body being formed by pores having a pore radius in the range from 500 to 2500 nm. Preference is given to from 40 to 90%, more preferably from 45 to 80%, in particular from 50 to 70%, of the pore volume of the shaped catalyst body being formed by pores having a pore radius in the range from 5 to 50 nm.

The combination of relatively large pores in the range from 700 to 2000 nm with small pores in the range from to 30 nm has been found to be advantageous, in particular for the reactions described here, for example hydrogenation. Without being tied to a theory, it is presumed that the small pores result in a large surface area available for the reactions and the large pores promote mass transfer of starting materials to the active sites and of products away from the active sites.

The tableted shaped catalyst body produced by the process of the invention preferably has a pore volume in the range from 0.1 to 0.6 $cm^3/g$ more preferably in the range from 0.13 to 0.40 $cm^3/g$, particularly preferably in the range from 0.15 to 0.25 $cm^3/g$.

The after-calcined shaped catalyst body produced by the process of the invention preferably has a pore volume in the range from 0.15 to 0.70 $cm^3/g$, more preferably in the range from 0.17 to 0.50 $cm^3/g$, particularly preferably in the range from 0.19 to 0.28 $cm^3/g$.

The reduced shaped catalyst body produced by the process of the invention preferably has a pore volume in the range from 0.20 to 0.80 $cm^3/g$, more preferably in the range from 0.22 to 0.70 $cm^3/g$, particularly preferably in the range from 0.25 to 0.35 $cm^3/g$. When the pore volume of the reduced shaped catalyst body is to be determined, the measurement is preferably carried out on the shaped catalyst body in the dry stabilized form.

The pore volume of the pellets before after-calcination is preferably smaller than the pore volume of the after-calcined pellets and the pore volume of the after-calcined pellets is preferably less than or equal to the pore volume of the reduced pellets.

In a further embodiment, the pore volume of the tableted shaped catalyst body of the invention is from 0.15 to 0.25 $cm^3/g$, the pore volume of the after-calcined shaped catalyst body is from 0.19 to 0.28 $cm^3/g$ and the pore volume of the reduced shaped catalyst body is from 0.25 to 0.35 $cm^3/g$.

In a particularly preferred embodiment, the shaped catalyst body of the invention is in reduced form and in the dry stabilized form has a pore volume in the range from 0.20 to 0.80 cm³/g, preferably in the range from 0.22 to 0.70 cm³/g, particularly preferably in the range from 0.25 to 0.35 cm³/g.

The reduced shaped catalyst body produced by the process of the invention preferably has a carbonate content of 8% by weight or less, particularly preferably 5% by weight or less, for example from 0.5 to 4% by weight.

The shaped catalyst body produced by the process of the invention preferably has a carbonate content of from 0.5 to 4% by weight, in particular from 1.0 to 2% by weight, before reduction. In a further embodiment, the present invention provides a tableted shaped Cu—Al catalyst body, in particular a tableted shaped Cu—Al—Mn catalyst body, which in reduced and stabilized form has a pore volume, measured by the Hg intrusion method in accordance with DIN 66133, in the range from 0.20 to 0.80 cm³/g, preferably from 0.22 to 0.70 cm³/g, particularly preferably from 0.25 to 0.35 cm³/g.

The shaped catalyst body of the invention preferably has a bimodal pore radius distribution, measured by the Hg intrusion method in accordance with DIN 66133, having a first maximum in the range from 10 to 30 nm, in particular in the range from 15 to 25 nm, and/or a second maximum in the range from 500 to 2500 nm, in particular in the range from 700 to 2000 nm.

The shaped catalyst body of the invention preferably has a pore radius distribution in which from 5 to 30%, more preferably from 10 to 25%, in particular from 15 to 25%, of the pore volume is formed by pores having a pore radius in the range from 500 to 2500 nm, and from 20 to 60%, more preferably from 30 to 55%, in particular from 35 to 50%, of the pore volume is formed by pores having a pore radius in the range from 5 to 50 nm.

The invention further provides a reduced tableted shaped catalyst body containing copper, aluminum and optionally a transition metal selected from the group consisting of Mn, Zn, Ce, Zr and mixtures thereof, in particular Mn. This shaped catalyst body preferably has a pore volume, determined by the Hg intrusion method in accordance with DIN 66133, in the range from 0.20 to 0.80 cm³/g, more preferably in the range from 0.22 to 0.70 cm³/g, particularly preferably in the range from 0.25 to 0.53 cm³/g. It preferably has a bimodal pore radius distribution in which from 5 to 30%, more preferably from 10 to 25%, in particular from 15 to 25%, of the pore volume of the shaped catalyst body is formed by pores having a pore radius in the range from 500 to 2500 nm, and/or from 20 to 60%, more preferably from 30 to 55%, in particular from 35 to 50%, of the pore volume of the shaped catalyst body is formed by pores having a pore radius in the range from 5 to 50 nm.

The shaped catalyst bodies of the invention are suitable for use in numerous reactions. Possible reactions include synthesis gas reactions, methanol syntheses, a Fischer-Tropsch synthesis, pyridine syntheses, ester hydrogenolyses, amination reactions, N-alkylations, hydrogenations of nitriles to amines, hydrogenation of acrylonitrile, hydrogenation of fatty acid esters, hydrogenation of diesters to diols (in particular maleic esters), hydrogenation of sugars to polyols, alkylation of a phenol by means of an alcohol, amination of an alcohol, dehydrogenation of an alcohol, hydrogenation of an aldehyde, hydrogenation of an amide, hydrogenation of a fatty acid, e.g. by esterification and subsequent hydrogenolysis, selective hydrogenation of a fat, selective hydrogenation of an oil, hydrogenation of a nitrile, hydrogenation of a nitroaromatic hydrocarbon, hydrogenation of a ketone, hydrogenation of furfural, hydrogenation of an ester and hydrogenation of carbon monoxide to form methanol.

In a preferred embodiment, the catalysts produced by the process of the invention are used for the hydrogenation of carbonyl compounds, in particular for the hydrogenation of aldehydes, ketones, carboxylic acids and/or esters thereof or dicarboxylic acids and/or diesters thereof, very particularly preferably for the hydrogenation of fatty acid esters, in particular alkyl esters of fatty acids, preferably methyl esters of fatty acids or maleic esters.

The catalyst of the invention is particularly suitable for the upflow-mode hydrogenation of carboxylic acids, preferably fatty acids or fatty acid mixtures having from 5 to 24 carbon atoms and/or esters thereof, optionally in admixture with alcohols, to form the corresponding fatty alcohols. Here, the fatty acids of fatty acid mixtures can be esterified in-situ by means of alcohols present in the reaction mixture. Preferred alcohols present in the reaction mixture are fatty alcohols or mixtures of fatty alcohols having from 5 to 24 carbon atoms. Particular preference is given to using the above-described catalyst for the hydrogenation of methyl esters of fatty acids.

EXAMPLES

Figure 1:
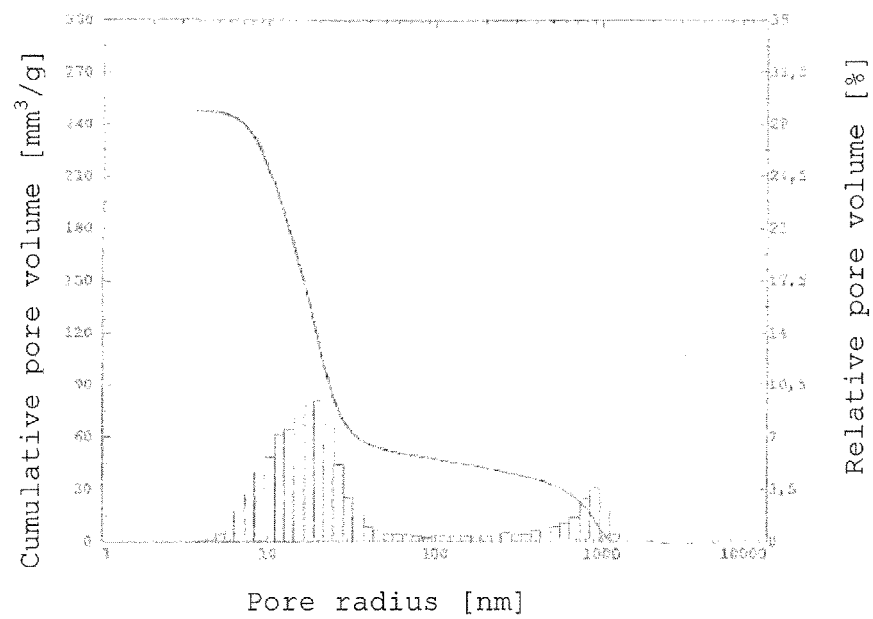
FIG. 1 shows the pore radius distribution, measured using the Hg intrusion method in accordance with DIN 66133, of catalyst 1A as per example 5 after after-calcination but before reduction.
Figure 2:
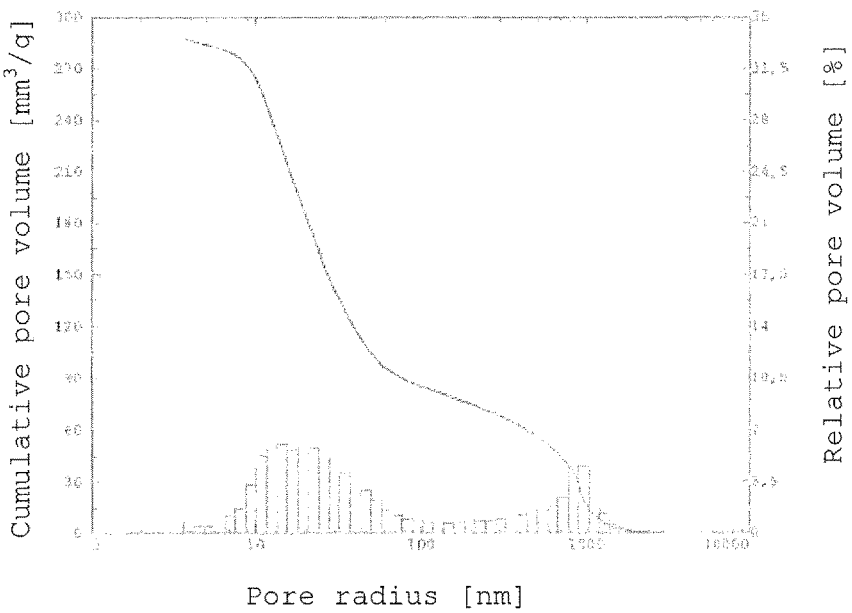
FIG. 2 shows the pore radius distribution, measured by the Hg intrusion method in accordance with DIN 66133, of catalyst 1A as per example 5 after after-calcination and reduction by means of 5% by volume of hydrogen in nitrogen at 200° C. for 4 hours.

The invention is illustrated by the following, nonlimiting examples. Even when these examples describe specific embodiments of the invention, they serve merely to illustrate the invention and should not be interpreted as restricting the invention in any way. As a person skilled in the art will know, numerous modifications can be made to these embodiments without going outside the scope of protection of the invention as defined by the accompanying claims.

Determination of Physical Parameters

The physical parameters described here are, unless indicated otherwise, determined as follows:

Conductivity is determined in accordance with DIN 38404, part 8.

Lateral compressive strength is determined in accordance with DIN EN 1094-5.

Remaining loss on ignition is determined in accordance with DIN EN 196-2.

Pore volume and pore radius distribution are determined by the Hg intrusion method in accordance with DIN 66133.

Carbonate content is determined in accordance with DIN ISO 10693.

Example 1 (Production of the Uncalcined Material)

The production of the uncalcined material is carried out via precipitation of the metal nitrates by means of sodium carbonate to form the carbonates thereof, and the precipitate is subsequently filtered off, washed and spray dried.

Solution 1 is produced from 617 g of $Cu(NO_3)_2 \cdot 3H_2O$, 106 g of $Mn(NO_3)_2 \cdot 4H_2O$, 875 g of $Al(NO_3)_3 \cdot 9H_2O$ and 5 l of $H_2O$. Solution 2 is produced from 850 g of $Na_2CO_3$ and 3.8 l of $H_2O$. The two solutions are heated to 80° C. and stirred. They are subsequently metered into a precipitation vessel. The pH in the precipitation vessel is 6.8. The volume flows of solutions 1 and 2 are set so that this pH is established. As soon as the two solutions have been consumed, the precipitate formed is filtered off and washed with water. The filter cake is then resuspended in about 1 l of water and spray dried. The resulting dried but still uncalcined powder is the starting material for the further preparations.

Example 2 (Production of the Calcined Material)

The calcined material is produced by calcining the uncalcined dried powder from example 1 at 750° C. in a convection furnace for 2 hours. The remaining loss on ignition of the calcined material at 1000° C. (LOI) is about 5% by weight.

Example 3 (Production of the Comparative Catalyst)

The comparative catalyst is produced by mixing 100 g of calcined powder produced as per example 2 with 3% by weight of graphite and subsequently tableting the mixture to form shaped bodies having a diameter of about 3 mm and a height of about 3 mm. The lateral compressive strength of the comparative catalyst is 85 N, determined in accordance with DIN EN 1094-5.

Example 4 (Production of Catalyst 1)

To produce catalyst 1, 75 g of calcined powder (from example 2) are mixed with 25 g of uncalcined powder (from example 1) and 3 g of graphite and tableted to form shaped bodies having a diameter of about 3 mm and a height of about 3 mm. The lateral compressive strength is 85 N.

Example 5 (Production of Catalyst 1a)

Catalyst 1A is produced in a manner analogous to catalyst 1, but the pellets are calcined at 750° C. in a convection furnace for 2 hours after tableting.

Example 6 (Production of Catalyst 2)

To produce the catalyst 2, 50 g of calcined powder (from example 2) are mixed with 50 g of uncalcined powder (from example 1) and 3 g of graphite and tableted to form shaped bodies having a diameter of about 3 mm and a height of about 3 mm. The lateral compressive strength is 75 N.

Example 7 (Production of Catalyst 2a)

Catalyst 2A is produced in a manner analogous to catalyst 2, but the pellets are calcined at 750° C. in a convection furnace for 2 hours after tableting.

Example 8 (Production of Catalyst 3)

To produce the catalyst 3, 25 g of calcined powder (from example 2) are mixed with 75 g of uncalcined powder (from example 1) and 3 g of graphite and tableted to form shaped bodies having a diameter of about 3 mm and a height of about 3 mm. The lateral compressive strength is 75 N.

Example 9 (Production of Catalyst 3a)

Catalyst 3A is produced in a manner analogous to catalyst 3, but the pellets are calcined at 750° C. in a convection furnace for 2 hours after tableting.

Example 10 (Production of Catalyst 4)

To produce the catalyst 4, 100 g of uncalcined powder (from example 1) and 3 g of graphite are mixed and tableted to form shaped bodies having a diameter of about 3 mm and a height of about 3 mm. The lateral compressive strength is 70 N.

Example 11 (Production of Catalyst 4a)

Catalyst 4A is produced in a manner analogous to catalyst 4, but the pellets are calcined at 750° C. in a convection furnace for 2 hours after tableting.

Example 12 (Activity Measurements)

The activity of the catalysts in respect of the hydrogenation of methyl esters of fatty acids (FAME) is examined. An electrically heated fixed-bed reactor having a reactor volume of 25 ml is used for this purpose. Methyl laurate (C12-methyl ester) is used for the test. To evaluate the conversion of the ester and the selectivity to the fatty alcohol or the formation of bi-products, the reaction product formed is analyzed by gas chromatography. The conversion is calculated from the molar amount of the ester used and the remaining molar amount of ester in the product.

For the analysis by gas chromatography, 6.0000 g of the product formed are mixed with 0.2000 g of 5-nonanol (internal standard). The sample is subsequently analyzed twice by means of a gas chromatograph.
Equipment Used:
GC: Agilent 7890A with FID
Column: ZB-1, 60 m×0.25 mm from Phenomenex
Software: EZ Chrom Elite Version 3.3.2 SP1
Test Conditions in the Hydrogenation of Methyl Laurate:
Temperature points: 240, 180, 160° C.,
Pressure: 280 bar
GHSV ($H_2$): 20000 $h^{-1}$
LHSV (ester): 1.4 $h^{-1}$ Table 1 shows the values for the conversions of C12-methyl ester obtained by the above-described method at 240° C., 180° C. and 160° C. for the comparative catalyst and the catalysts 1 to 4 and 1A to 4A (examples 4 to 11). The improved activity on the catalysts 1 to 4 and 1A to 4A compared to the comparative catalyst can clearly be seen, in particular at 160° C. As the values for the catalysts 1A, 2A, 3A and 4A show, a renewed improvement in the activity is obtained by means of an after-calcination.

TABLE 1

Conversions of C12-methyl ester at 240, 180 and 160° C.

| Catalysts | Ratio of uncalcined material to calcined material | Conversion of C12-methyl ester [%] | | |
|---|---|---|---|---|
| | | 240° C. | 180° C. | 160° C. |
| Comparative catalyst | 0/100 | 97.1 | 81 | 62.5 |
| Catalyst 1 | 25/75 | 97.9 | 83.9 | 72.4 |
| Catalyst 1A | 25/75, after-calcined | 99.5 | 98 | 81.8 |
| Catalyst 2 | 50/50 | 97.9 | 83 | 70 |
| Catalyst 2A | 50/50, after-calcined | 98.8 | 95.2 | 77.3 |
| Catalyst 3 | 75/25 | 97.8 | 82 | 67 |
| Catalyst 3A | 75/25, after-calcined | 98.3 | 93.5 | 75.6 |

TABLE 1-continued

Conversions of C12-methyl ester at 240, 180 and 160° C.

| Catalysts | Ratio of uncalcined material to calcined material | Conversion of C12-methyl ester [%] | | |
| --- | --- | --- | --- | --- |
| | | 240° C. | 180° C. | 160° C. |
| Catalyst 4 | 100/0 | 97.6 | 81 | 66 |
| Catalyst 4A | 100/0, after-calcined | 98.1 | 90.1 | 73.3 |

Table 2 shows the values for the carbonate content and the pore volume of the various catalysts after tableting but before an after-calcination, after tableting and after-calcination and also after tableting, after-calcination and reduction. Reduction was carried out at 200° C. for 4 hours using 5% by volume of hydrogen in nitrogen. The pore volume was determined by the mercury intrusion method in accordance with DIN 66133. Particularly after reduction, the shaped catalyst bodies according to the invention have a higher pore volume than the comparative catalyst.

TABLE 2

Carbonate content and pore volume

| | Carbonate content [%] | Pore volume [cm³/g] | | |
| --- | --- | --- | --- | --- |
| | | After tableting | After calcination | After reduction |
| Comparative catalyst | — | 0.15 | | 0.2 |
| Catalyst 1 | 2.3 | 0.13 | 0.24* | 0.29 |
| Catalyst 2 | 4.5 | 0.19 | 0.33* | 0.46 |
| Catalyst 3 | 6.8 | 0.24 | 0.36* | 0.5 |
| Catalyst 4 | 8.9 | 0.3 | 0.37* | 0.52 |

*values correspond to the catalysts 1A to 4A

The analytical data show that the carbonate content of the catalysts varies as a function of the proportion of uncalcined material.

It can be seen from table 1 that the catalysts produced according to the invention have a significantly increased conversion of methyl laurate compared to the comparative catalyst. This increase could be observed at all three temperatures selected, 160° C., 180° C. and 240° C. The proportion of unreacted C12-methyl ester could be reduced to less than one fifth (from 2.9% in the case of the comparative catalyst to 0.5% in the case of catalyst 1A).

In summary, it can therefore be said that an improvement in the economics, in particular an increase in the conversion to the target product, is achieved by means of the catalyst of the invention.

The invention claimed is:

1. A process for producing a tableted shaped catalyst body, which comprises the steps of:
    (a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate to give a dried precipitate, and
    (b) tableting of the dried precipitate obtained in step (a), wherein step (b) comprises:
        (b1) calcination of dried precipitate obtained in step (a) at a temperature in the range from 250 to 900° C., to give a calcined precipitate,
        (b2) mixing of dried precipitate obtained in step (a) with calcined precipitate obtained in step (b1) in a weight ratio of dried precipitate to calcined precipitate in the range from 2:98 to 98:2, to give a mixture, and
        (b3) tableting of the mixture obtained in step (b2).

2. The process according to claim 1, wherein a lubricant is added to the uncalcined precipitate obtained from step (a) or to the mixture obtained from step (b2) in an amount of from 0.1 to 5% by weight, based on the total weight of the composition to be tableted, before tableting.

3. The process according to claim 2, wherein the lubricant is added in an amount of from 0.5 to 5% by weight, based on the total weight of the composition to be tableted.

4. The process according to claim 2, wherein the lubricant is graphite.

5. The process according to claim 2, wherein the lubricant is added in an amount of from 1 to 4% by weight, based on the total weight of the composition to be tableted.

6. The process according to claim 1, wherein the pore volume of the tableted shaped catalyst body, determined by the Hg intrusion method in accordance with DIN 66133, is from 0.1 to 0.6 cm³/g.

7. The process according to claim 1, which comprises the following step:
    (c) after-calcination of the tableted shaped catalyst body at a temperature in the range from 250 to 900° C., to give an after-calcined shaped catalyst body.

8. The process according to claim 7, wherein the pore volume of the after-calcined shaped catalyst body, determined by the Hg intrusion method in accordance with DIN 66133, is from 0.15 to 0.70 cm³/g.

9. The process according to claim 8, wherein the pore volume of the after-calcined shaped catalyst body, determined by the Hg intrusion method in accordance with DIN 66133, is from 0.17 to 0.50 cm³/g.

10. The process according to claim 8, wherein the pore volume of the after-calcined shaped catalyst body, determined by the Hg intrusion method in accordance with DIN 66133, is from 0.19 to 0.4 cm³/g.

11. The process according to claim 7, wherein the step (c) takes places at temperature of about 750° C.

12. The process according to claim 7, which comprises the following step:
    (d) reduction of the tableted shaped catalyst body obtained from step (b) and/or the after-calcined shaped catalyst body obtained from step (c) to give a reduced shaped catalyst body.

13. The process according to claim 12, wherein reduction is effected by means of hydrogen.

14. The process according to claim 12, wherein reduction is carried out at a temperature in the range from 150° C. to 400° C.

15. The process according to claim 12, wherein reduction is carried out over a period of from 1 hour to 10 days.

16. The process according to claim 12, wherein
    (a) the reduced shaped catalyst body is covered with a liquid with exclusion of air after reduction, where the liquid is selected from the group consisting of isodecanol, fatty alcohols, hexadecane, 2-ethylhexanol, propylene glycol and mixtures thereof, or
    (b) a mixture of an oxygen-containing gas and an inert gas, wherein the oxygen-containing gas is oxygen and the inert gas is argon or nitrogen is fed into the reduction reactor containing the reduced shaped catalyst body, where the concentration of oxygen in the mixture during introduction is from 0.001% by volume to 50% by volume and is increased from about 0.02% by volume to about 21% by volume.

17. The process according to claim 7, wherein the step (c) takes place at a temperature in the range from 300 to 750° C.

18. The process according to claim 7, wherein the step (c) takes place at temperature in the range of 600 to 750° C.

19. The process according to claim 12, wherein reduction is carried out at a temperature in the range from 180° C. to 250° C.

20. The process according to claim 12, wherein reduction is carried out at a temperature in the range from 190° C. to 210° C.

21. The process according to claim 12, wherein reduction is carried out at, a temperature of about 200° C.

22. The process according to claim 12, wherein reduction is carried out over a period of from 2 hours to 72 hours.

23. The process according to claim 12, wherein reduction is carried out over a period of from 24 to 48 hours.

24. The process according to claim 1, wherein the precipitate obtained in step (a) has a carbonate content of up to 20% by weight inclusive, based on the total weight of the dried precipitate obtained in step (a).

25. The process according to claim 1, wherein the copper compound is selected from the group consisting of copper, copper oxide ($Cu_2O$ and/or CuO), copper nitrate, copper sulfate, copper carbonate, copper hydroxocarbonate, copper acetate, copper halides copper chloride, copper bromide or copper iodide and mixtures thereof.

26. The process according to claim 1, wherein the aluminum compound is selected from the group consisting of aluminum, aluminum hydroxide, aluminum oxide hydrate (boehmite), alkali metal aluminates, aluminum oxide ($Al_2O_3$), aluminum nitrate, aluminum sulfate, aluminum halides and mixtures thereof.

27. The process according to claim 1, wherein the transition metal compound is selected from the group consisting of Zn, Ti, Mn, Ni, Cr, Fe, Co, Mo, Ce and Zr and mixtures thereof.

28. The process according, to claim 1, wherein the carbonate-containing solution is obtained using at least one alkali metal carbonate, alkaline earth metal carbonate and/or ammonium carbonate and/or at least one alkali metal hydrogen carbonate, alkaline earth metal hydrogen carbonate and/or ammonium hydrogen carbonate.

29. The process according to claim 1, wherein step (b1) calcination of dried precipitate obtained in step (a) at a temperature in the range from 300 to 750° C., to give a calcined precipitate.

30. The process according to claim 1, wherein step (b1) calcination of dried precipitate obtained in step (a) at a temperature in the range from 600 to 750° C., to give a calcined precipitate.

31. The process according to claim 1, wherein the weight ratio of dried precipitate to calcined precipitate is in the range of from 10:90 to 90:10 to give a mixture.

32. The process according to claim 1, wherein the weight ratio of dried precipitate to calcined precipitate is in the range of from 15:85 to 85:15 to give a mixture.

33. The process according to claim 1, wherein the weight ratio of dried precipitate to calcined precipitate is in the range of from 20:80 to 50:50 to give a mixture.

34. The process according to claim 1, wherein the pore volume of the tableted shaped catalyst body, determined by the Hg intrusion method in accordance with DIN 66133, is from 0.13 to 0.40 $cm^3/g$.

35. The process according to claim 1, wherein the pore volume of the tableted shaped catalyst body, determined by the Hg intrusion method in accordance with DIN 66133, is from 0.15 to 0.25 $cm^3/g$.

36. The process according to claim 1, wherein the precipitate obtained in step (a) has a carbonate content range from 5% by weight to 18% by weight, based on the total weight of the dried precipitate obtained in step (a).

37. The process according to claim 1, wherein the precipitate obtained in step (a) has a carbonate content in the range from 6% by weight to 15% by weight, based on the total weight of the dried precipitate obtained in step (a).

38. The process according to claim 1, wherein the precipitate obtained in step (a) has a carbonate content in the range from 8 to 12% by weight, based on the total weight of the dried precipitate obtained in step (a).

39. The process according to claim 1, wherein the copper compound is selected from the group consisting of copper oxide, copper nitrate, copper chloride, copper carbonate, copper hydroxocarbonate, copper acetate, copper sulfate and mixtures thereof.

40. The process according to claim 1, wherein the aluminum compound is selected from the group consisting of aluminum nitrate, aluminum hydroxide, aluminum oxide hydrate, aluminum chloride, sodium aluminate, aluminum oxide and mixtures thereof.

41. The process according to claim 1, wherein the transition metal compound is selected from the group consisting of Mn, Zn, Ce, Zr and mixtures thereof.

42. The process according to claim 1, wherein the transition metal compound is from among compounds of Mn.

43. The process according to claim 1, wherein the carbonate-containing solution is obtained using sodium carbonate and/or sodium hydrogen carbonate.

44. A process for producing a tableted shaped catalyst body, which comprises the steps of:
  (a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate to give a dried precipitate, and
  (b) tableting of the dried precipitate obtained in step (a), wherein the precipitate obtained in step (a) contains at least 5% by weight of Cu hydroxocarbonate.

45. A process for producing a tableted shaped catalyst body, which comprises the steps of:
  (a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate to give a dried precipitate,
  (b) tableting of the dried precipitate obtained in step (a);
  (c) after-calcination of the tableted shaped catalyst body at a temperature in the range from 250 to 900° C., to give an after-calcined shaped catalyst body
  wherein the pore volume of the tableted shaped catalyst body, determined by the Hp intrusion method in accordance with DIN 66133, is from 0.1 to 0.6 $cm^3/g$; and (d) reduction of the tableted shaped catalyst body obtained from step (b) and/or the after-calcined shaped catalyst body obtained from step (c) to give a reduced shaped catalyst body, wherein (a) the reduced shaped catalyst body is covered with a liquid with exclusion of air after reduction, where the liquid is isodecanol.

46. A process for producing a tableted shaped catalyst body, which comprises the steps of:
(a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate to give a dried precipitate, (b) tableting of the dried precipitate obtained in step (a),
(c) after-calcination of the tableted shaped catalyst body at a temperature in the range from 250 to 900° C., to give an after-calcined shaped catalyst body,
wherein the pore volume of the tableted shaped catalyst body, determined by the Hg intrusion method in accordance with DIN 66133, is from 0.1 to 0.6 cm$^3$/g, and (d) reduction of the tableted shaped catalyst body obtained from step (b) and/or the after-calcined shaped catalyst body obtained from step (c) to give a reduced shaped catalyst body, wherein
(a1) the reduced shaped catalyst body is covered with a liquid with exclusion of air after reduction, where the liquid is selected from the group consisting of isodecanol, fatty alcohols, hexadecane, 2-ethylhexanol, propylene glycol and mixtures thereof, or (b1) a mixture of an oxygen-containing gas and an inert gas, wherein the oxygen-containing gas is oxygen and the inert gas is argon or nitrogen, is fed into the reduction reactor containing the reduced shaped catalyst body, where the concentration of oxygen in the mixture during introduction is from 0.001% by volume to 50% by volume and is increased from about 0.02% by volume to about 21% by volume.

47. A process for producing a tableted shaped catalyst body, which comprises the steps of:
(a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate to give a dried precipitate, and
(b) tableting of the dried precipitate obtained in step (a) wherein the precipitate obtained in step (a) contains from 10 to 80% by weight, of Cu hydroxocarbonate.

48. A process for producing a tableted shaped catalyst body, which comprises the steps of:
(a) combining of (i) at least one aqueous solution of copper compounds, aluminum compounds and optionally transition metal compounds and (ii) at least one aqueous carbonate-containing solution to form a precipitate, isolation of the precipitate, optionally washing of the isolated precipitate and drying of the isolated precipitate to give a dried precipitate, and
(b) tableting of the dried precipitate obtained in step (a), wherein the precipitate obtained in step (a) contains from 15 to 70% by weight, of Cu hydroxocarbonate.

* * * * *